US006846996B2

United States Patent
Kent et al.

(10) Patent No.: US 6,846,996 B2
(45) Date of Patent: Jan. 25, 2005

(54) PUSHBUTTON MECHANICAL LIMITER SWITCH INCLUDING MOVABLE CONTACT WITH CONDUCTIVE RADIAL SEGMENT LOCATED IN SERRATED HOUSING PASSAGEWAY

(75) Inventors: Harold B. Kent, Portola Valley, CA (US); James J. Levante, Redwood City, CA (US); Aaron T. Fine, Alviso, CA (US); Joseph R. Layton, Sunnyvale, CA (US)

(73) Assignee: Medconx, Inc., Santa Clara, CA (US)

( * ) Notice: Subject to any disclaimer, the term of this patent is extended or adjusted under 35 U.S.C. 154(b) by 0 days.

(21) Appl. No.: 10/739,252

(22) Filed: Dec. 17, 2003

(65) Prior Publication Data

US 2004/0129551 A1 Jul. 8, 2004

Related U.S. Application Data

(60) Provisional application No. 60/434,297, filed on Dec. 17, 2002.

(51) Int. Cl.[7] .............................. H01H 1/12; H01H 1/34; H01H 3/12; H01H 13/50
(52) U.S. Cl. .................... 200/276.1; 200/290; 200/520; 200/535
(58) Field of Search ........................... 200/51 R–51.17, 200/275, 276, 276.1, 290, 520–536, 8 R, 8 A

(56) References Cited

U.S. PATENT DOCUMENTS

| 3,226,496 | A | * | 12/1965 | Seabury, Jr. ................. 200/8 R |
| 3,548,137 | A | * | 12/1970 | Farrell et al. ................. 200/276 |
| 4,284,862 | A | * | 8/1981 | Overman et al. ........... 200/276 |
| 4,313,685 | A | * | 2/1982 | Stahl et al. .................. 200/520 |
| 4,533,803 | A | * | 8/1985 | Beller et al. ................. 200/290 |
| 2003/0233087 | A1 | | 12/2003 | Chen ........................... 606/41 |

* cited by examiner

*Primary Examiner*—James R. Scott
(74) *Attorney, Agent, or Firm*—Burns, Doane, Swecker & Mathis, LLP

(57) ABSTRACT

A mechanical limiter switch for use in a medical or surgical device has a substantially cylindrically shaped housing with a perimeter and an opening in an axial direction. The housing has a pattern along the perimeter. A spring is mounted in the opening along the axial direction, and is pre-stressed for movement in a radial direction and pre-stressed for movement in the axial direction. The spring has a radial member protruding through the pattern of the housing. A plunger is mounted in the opening along the axial direction, abutting the spring for urging the spring in the axial direction and for moving the member in the pattern along the perimeter. After a pre-determined number of activations of the plunger in the axial direction, the member will come to a terminating position and will either contact a pin to establish electrical continuity or at the terminating position break electrical continuity.

47 Claims, 8 Drawing Sheets

PUSHBUTTON MECHANICAL LIMITER SWITCH INCLUDING MOVABLE CONTACT WITH CONDUCTIVE RADIAL SEGMENT LOCATED IN SERRATED HOUSING PASSAGEWAY

This application claims the priority of provisional application 60/434,297 filed on Dec. 17, 2002.

TECHNICAL FIELD

The present invention relates to a mechanical limiter switch and more particularly to a limiter switch for use in a medical or surgical device wherein said switch limits the operation of the device after a pre-determined number of operations.

BACKGROUND OF THE INVENTION

Current methods to limit the number of uses of electrical devices, such as those used in surgical procedures or other health or medical related applications have relied upon regulatory actions, such as regulations promulgated by the United Stated FDA and the European Regulatory body (EUR). Clearly, this method relies upon the user to adhere to those regulations subject to penalties for non-compliance. Thus, this is only a self-adhering method to limit the use of these devices.

Minimally invasive surgical devices comprise most of the electrical devices whose use is limited by regulatory action. These devices can be expensive and reimbursement for their use can be tightly controlled by health insurance. Further, in many parts of the lesser-developed countries of the world, availability can be limited. These devices are regulated to limit the amount of usage because of efficacy, sterility, and to limit cross contamination etc. Within the US, tracking of the devices by lot and serial number is required in the entire distribution channel to the end use. The tracking system, along with the threat of lawsuit, creates a barrier to misuse. However, outside of the US where the tort system is not as well developed, multiple misuses can occur with greater frequency. These factors present a potential liability for the manufacturer of these devices along with the associated tarnishing of goodwill and reputation to the manufacturer.

Another prior art method has been the implementation of electrical circuits with associated electronic integrated circuits, and associated software to limit the use of the device. This "solution" has at least two limitations. First, they cannot be used to retrofit existing devices easily. Since such devices must work with an electronic controller that manages the device, the retrofitting of the existing devices may necessitate a retrofit of the controller. Second, one of the most effective method of sterilizing these devices is through the use of gamma radiation (or x-ray). X rays potentially can destroy integrated circuits and/or alter the content of memory and integrated circuits, thereby altering the software in an uncontrollable manner.

Hence, there is a need for a limiter switch that can be used in a surgical or medical device to limit the amount of uses of such devices that is both easy to use and is immune to most sterilization techniques, and is stable in all known forms of sterilization, e.g. Gamma, ETO, E-Beam, AutoClave, etc.

SUMMARY OF THE INVENTION

Accordingly, in the present invention, a limiter switch is comprised of a substantially cylindrically shaped housing having a perimeter and an opening in an axial direction. The housing has a pattern on the perimeter. A spring is mounted in the opening along the axial direction. The spring has a radial member protruding through the pattern. A plunger is mounted in the opening along the axial direction, abutting the spring for urging the spring in the axial direction and for moving the member rotationally in the pattern along the perimeter. After a pre-determined number of activations of the plunger in the axial direction, the member will either contact a contact pin to establish an electrical continuity or come to a terminating position that breaks electrical continuity.

BRIEF DESCRIPTION OF THE DRAWINGS

FIG. 6b is a side-enlarged view of the pattern shown in FIG. 6a.

FIG. 9b is a fully assembled perspective view of the embodiment of the switch shown in FIG. 9a.

FIG. 10b is a fully assembled perspective view of the embodiment of the switch shown in FIG. 10a.

FIG. 11b is a fully assembled perspective view of the embodiment of the switch shown in FIG. 11a.

DETAILED DESCRIPTION OF THE PREFERRED EMBODIMENTS

Figure 1:
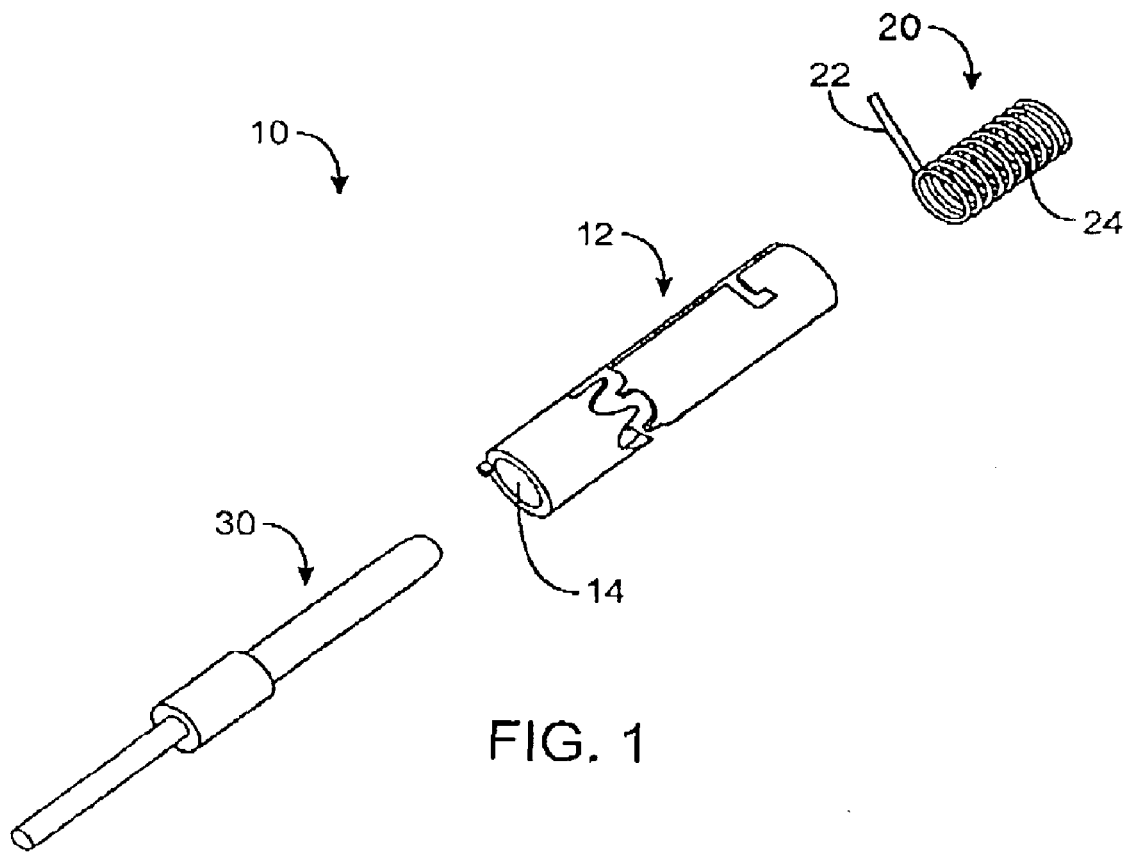
FIG. 1 is an exploded view of one embodiment of a mechanical limiter switch of the present invention.

Referring to FIG. 1, there is shown an exploded view of a mechanical limiter switch 10 of the present invention. The switch 10 comprises a housing 12, which is substantially cylindrically shaped and has an outer perimeter, and an opening 14 in an axial direction. The housing 12 has a pattern 16 along its perimeter. In a preferred embodiment, the pattern 16 is zigzag shaped; having crests 16a and troughs 16b (shown in FIG. 6b). The housing 12 also has a notch 18 (shown in FIG. 2). A spring 20 is positioned axially in the opening 14 of the housing 12. The spring 20 has a member 22 near a first end, which extends radially from the spring 20. The spring 20 has a second end 24. The spring 20 is mounted in the axial opening 14 of the housing 12 such that the second end 24 is anchored in the notch 18, and the member 22 protruding through the pattern opening 16 of the housing 12. When the spring 20 is so positioned, it is pre-tensioned in the radial direction. Thus, as the spring 20 is placed in the axial opening 14, the member 22 is positioned to protrude through the pattern opening 16. The spring 20 is then radially twisted and axially compressed to pre-tension the spring 20, and the second end 24 is then anchored at the notch 18. In one embodiment, the second end 24 also comprises a radial protrusion. Thus, the spring 20 is anchored by placing the second end 24 through the notch 18. Finally, the switch 10 comprises a plunger 30. The plunger 30 moves in an axial direction in the axial opening 14 of the housing 12 and urges or acts against the spring 20.

Figure 2:
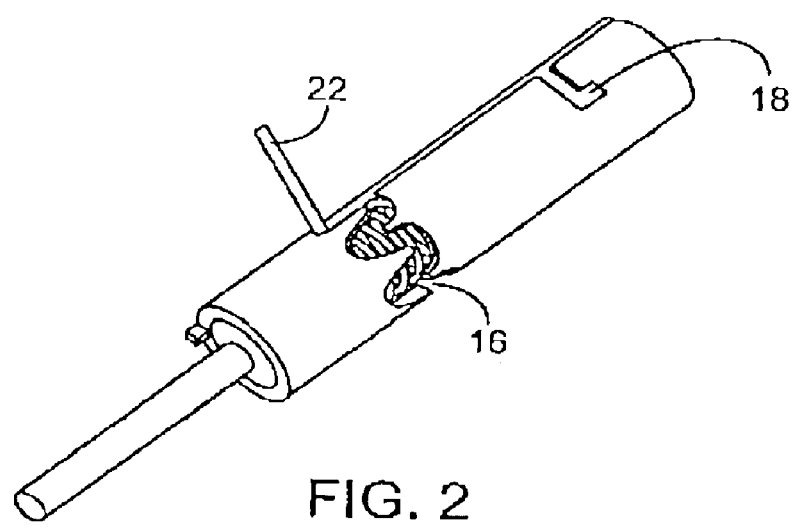
FIG. 2 is perspective view of a fully assembled mechanical limiter switch of the embodiment shown in FIG. 1.
Figure 3A:
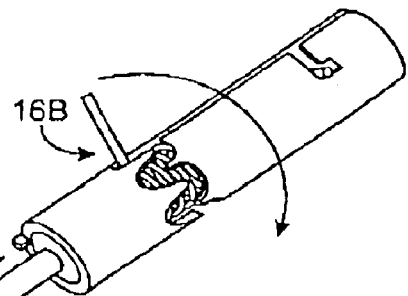
FIGS. 3a–3f are perspective views showing the operation of the switch shown in FIG. 2.
Figure 3B:
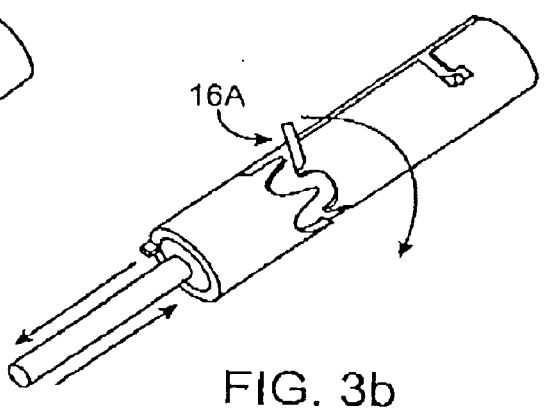
Figure 3C:
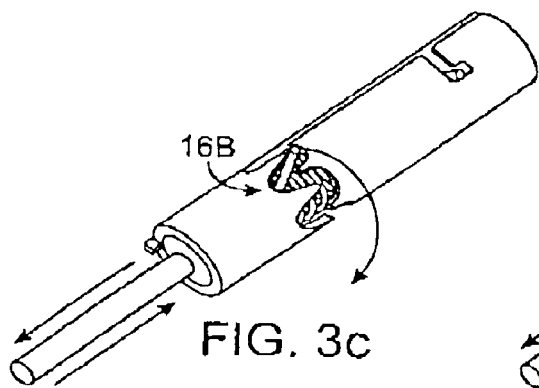
Figure 3D:
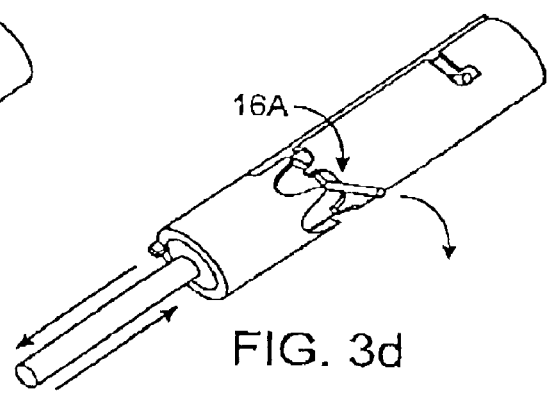
Figure 3E:
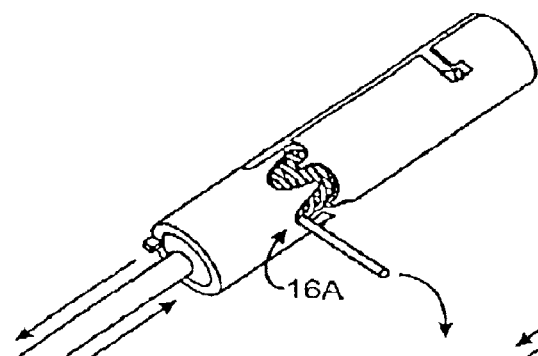
Figure 3F:
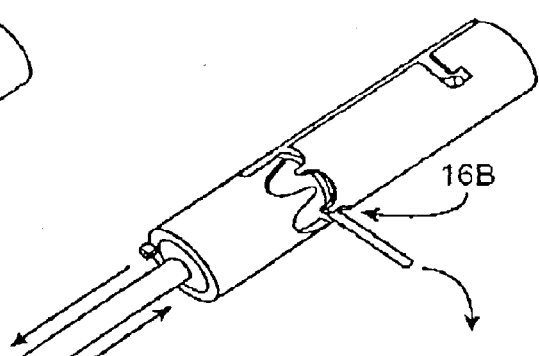
Figure 4:
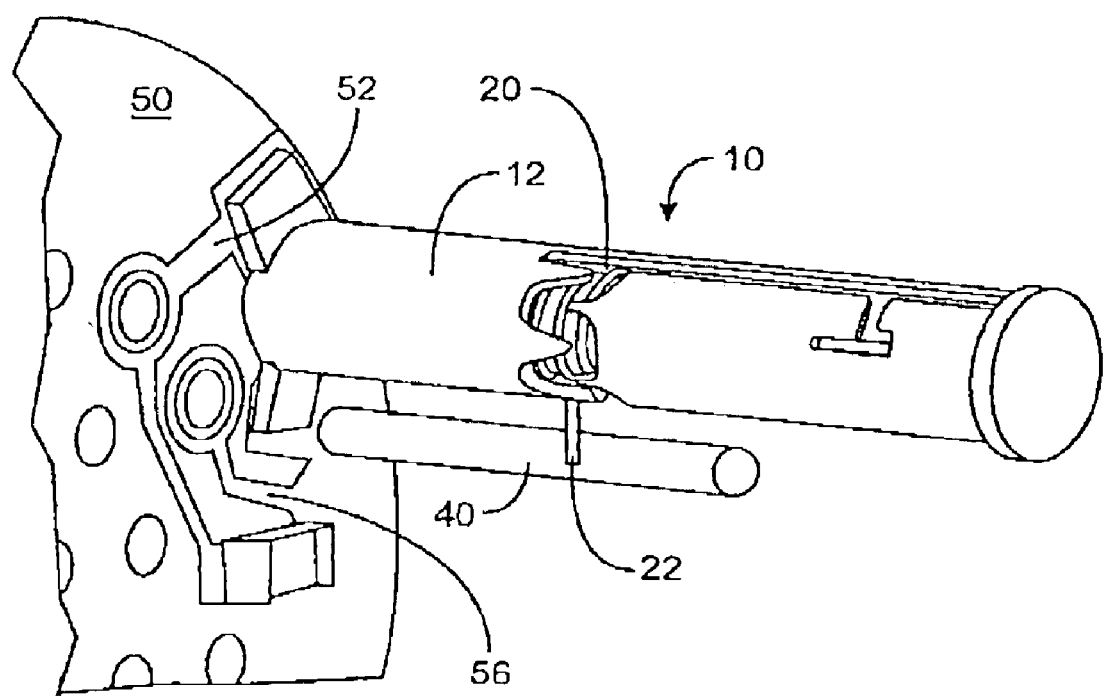
FIG. 4 is a perspective view of the switch shown in FIG. 2 mounted on a substrate to establish electrical continuity at a terminating position of the switch.

When fully assembled, the switch 10 is shown in a perspective view in FIG. 2. The operation of the switch 10 can be seen by reference to FIGS. 3a–3f. FIG. 3a shows the switch 10 in a first position at the start of operation in which the member 22 rests in the first trough 16b of the pattern 16. After plunger 30 is moved in an axial direction urging against the spring 20, the member 22 traverses along the pattern 16 in an axial direction and in a radial direction, due to the pre-tension of the spring 20. The result of the plunger 30 pressed to the fullest extent against the spring 20 is shown in FIG. 3b in which the member 22 rests against the crest 16a in the pattern 16. When force is released from the plunger 30 urging against the spring 20, the axial compression force of the spring 20 pushes the plunger 30 back. In addition, because the spring 20 is pre-stressed in the radial direction, the member 22 would then traverse the pattern 16 causing the spring 20 to rotate. This brings the member 22 of the spring 20 to rest against the next trough 16b in the pattern 16. The result is shown in FIG. 3c. This completes one operation of the switch 10. The number of operations that the switch 10 can operate is predetermined by the number of crests 16a and troughs 16b of the pattern 16. Thus, another operation of the switch 10 would causes the member to be pressed to another crest 16a in the pattern 16 (See FIG. 3d), followed by the member 22 coming to rest against another trough 16b (See FIG. 3e) in the pattern 16. This completes another use of the switch 10. Another use of the switch 10 causes the member 22 to move in the pattern 16 to another crest 16a (See FIG. 3f) followed by a return to another trough 16b in the pattern 16 (See FIG. 4), to the final position. At the final position, the member 22 may make electrical contact to establish electrical continuity with a contact pin 40, as shown in FIG. 4.

The switch 10 can be used in a medical or surgical device; the switch 10 is mounted on a substrate 50. Preferably, the substrate 50 is a printed circuit board connector of the type disclosed in U.S. patent application Ser. No. 10/171,698 filed on Jun. 17, 2002, assigned to the present assignee, whose disclosure is incorporated by reference in its entirety. As seen in FIG. 4, the switch 10 is mounted on the printed circuit board connector 50. In the embodiment shown in FIG. 4, the spring 20 is made of metal, the contact pin 40 is made of metal, and the housing 12 is also made of metal. The housing 12 can be mounted on the substrate 50 by press fit, surface mount, through-hole mounting, "mosquito" clip mounting, adhesive mounting, molded-in mounting, or snap-fit mounting into a preformed shape. The spring 20 and the housing 12 are electrically connected to the electrical tracing 52 on the printed circuit board connector 50. The contact pin 40 is also mounted on the printed circuit board connector 50 spaced apart from the switch 10. The contact pin 40 is also electrically connected to an electrical tracing 56 on the printed circuit board connector 50. The printed circuit board connector 50 can be used in a medical/surgical hand piece or electrical connector 70 to perform various medical/surgical procedures. The hand piece or receptacle electrical connector 70 is typically electrically connected to a medical/surgical connector 72 (shown in FIG. 8).

When the hand piece or receptacle electrical connector 70 is connected to the plug connector 72, the device can be used to perform the medical/surgical procedure. With the hand piece or receptacle electrical connector 70 is connected to the plug connector 72, the plug connector 72 urges the plunger 30 pushing it to cause the member 22 to come to rest at a crest position 16a in the pattern 16. After the procedure or one unplugging cycle, the hand piece or receptacle electrical connector 70 is removed from the plug connector 72. This causes the plunger 30 to return the member 22 to a trough position 16b in the pattern. The hand piece or receptacle electrical connector 70 is then sometimes subject to a sterilizing procedure. After the hand piece or receptacle electrical connector 70 is sterilized or just plugged in again, it is connected back to the plug connector 72, causing the plug connector 72 to urge the plunger 30 against the spring 20, and causing the member 22 to be pushed to another crest position 16a in the pattern 16. This action of connecting or reconnecting the hand piece or receptacle electrical connector 70 to the plug connector 72 causing the plug connector 72 to push the plunger 30 causing the member 22 to move to a crest position 16a in the pattern 16, and removing the hand piece 70 from the or receptacle electrical connector connector 72 causing the member to move to a trough position 16b repeats until the member 22 comes to contact against the contact pin 40 (as shown in FIG. 4). At that position, electrical contact is established between the electrical trace 52, the housing 12, the member 22 of the spring 20, to the contact pin 40 to the electrical tracing 56. When contact is so made, the switch 10 can cause electrical continuity to be established. This could cause the controller 72 not to provide any power to the hand piece or receptacle electrical connector 70. This would then cause the hand piece or receptacle electrical connector 70 to stop functioning. The number of operations that the hand piece or receptacle electrical connector 70 can be used is determined by the number of crests and troughs in the pattern 16, which are pre-set at the factory when the hand piece or receptacle electrical connector 70 is first assembled.

Figure 5A:
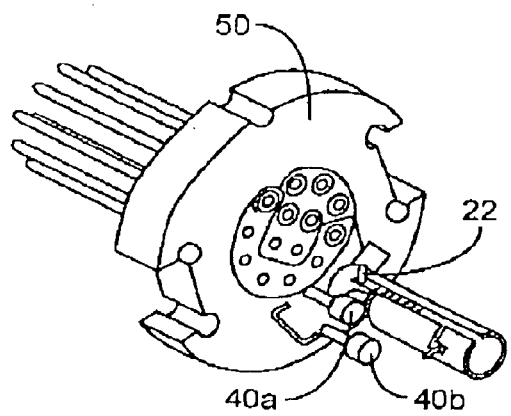
FIGS. 5a–5e are perspective views showing the operation of the switch shown in FIG. 2 mounted on a substrate wherein the switch at the terminating position breaks electrical continuity.
Figure 5B:
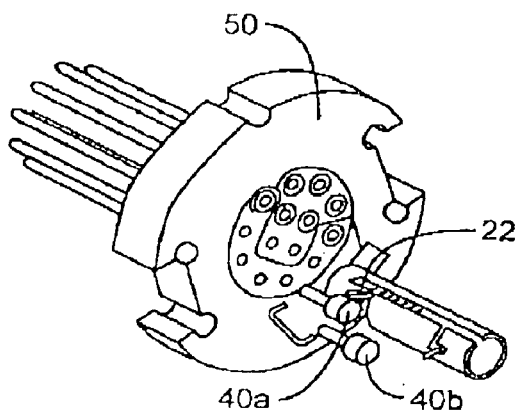
Figure 5C:
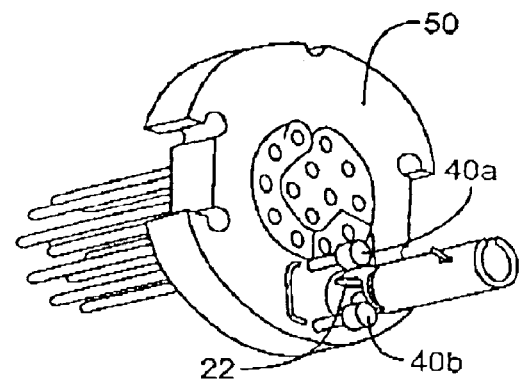
Figure 5D:
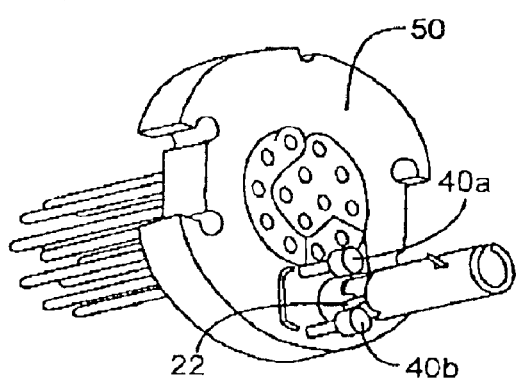
Figure 5E:
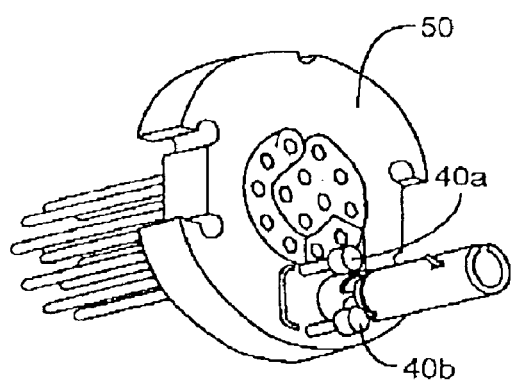

Referring to FIGS. 5a–5e there is shown a series of perspective views of a switch 10 mounted on a substrate 50 with the member 22 moving to contact a plurality of contact pins 40(a–b). Each of the contact pins 40 has a bulge like portion at its end. The bulge like portion is positioned near the crest portion 16a of the pattern 16. FIG. 5a shows the initial position of the switch 10 in which the member 22 is not in contact with either of the contact pins 40a or 40b. When the plunger 30 is urged against the spring 20, the member 22 is moved axially and radially to the position shown in FIG. 5b. At that location, the member 22 contacts the bulge like portion of the first contact pin 40a establishing electrical continuity with the contact pin 40a. When the hand piece 70 is disconnected from the plug connector 72, the member 22 traverses to a trough portion 16b of the pattern 16, as shown in FIG. 5c. At that location, the member 22 does not contact either of the contact pins 40a or 40b. When the hand piece 70 is connected to the plug connector 72 again, the plunger 30 is urged against the spring 20 causing the member 22 to move to the next crest position 16a of the pattern 16. At that location, the member 22 contacts the bulge like portion of the second contact pin 40b, thereby establishing electrical continuity. Finally, when the hand piece or receptacle electrical connector 70 is removed from the plug connector 72, the member 22 traverses to the terminating position, wherein the member 22 does not make electrical contact with either contact pins 40a or 40b. Thus, in this embodiment, through a change in the shape of the contact pin 40, and the location, and the pattern 16, the switch can be used to establish electrical continuity during the positions in which the plunger 30 is activated, and to break electrical continuity when the member reaches the terminating position.

Figure 6A:
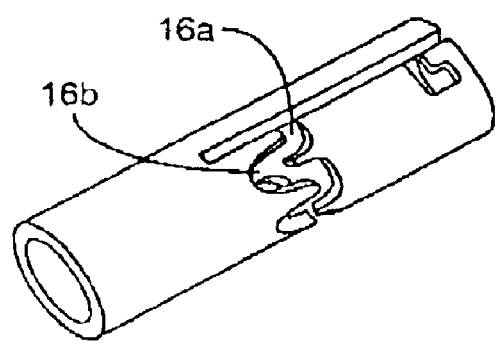
FIG. 6a is a perspective-enlarged view of the housing of the switch shown in FIG. 2, and the pattern through which the member traverses.
Figure 6B:
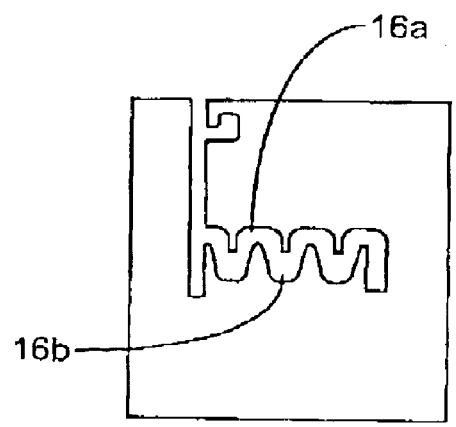

Referring to FIG. 6a there is shown an exploded view of the housing 12 with the pattern 16. The pattern 16 (as shown in FIG. 6b) as previously discussed has one or more crests 16a and one or more troughs 16b. The number of crests 16a and troughs 16b determines the number of activations of the switch 10 at the end of which either electrical continuity is established or electrical continuity is broken. The distance between each crest 16a and adjacent trough 16b is determinative of the distance of the throw of the plunger 30 by which the plunger 30 must move to activate each operation. This distance is further determinative of the amount of force required for the activation of the switch 10. The distance and depth of the pattern also make it possible to require that the connector be fully engaged to make electrical contact with the sensing resistor pins which can be shortened.

Figure 7:
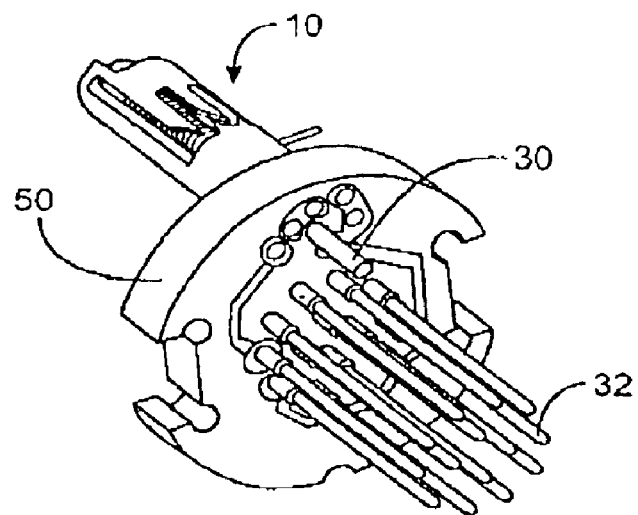
FIG. 7 is a perspective view of the switch shown in FIG. 2 mounted on a substrate, showing the plunger through the substrate and the relationship of the size of the plunger to the other signal connectors of the substrate.

Referring to FIG. 7 there is shown a perspective view of the underside of the substrate 50 on which the switch 10 is mounted to one side. As shown in FIG. 7, the substrate 50 has a plurality of electrical signal pin connectors 32 mounted on the underside. The plunger 30 passes through the opening in the substrate 50. The length of the plunger 30 can be chosen to be shorter than the other electrical signal pin connectors 32. This feature assures that the user must fully engage the hand piece or receptacle electrical connector 70 to the plug connector 72, and move the plunger 30 thereby activating the switch 10. This thwarts any attempt to defeat the limitation of the activation of the switch 10.

Figure 8:
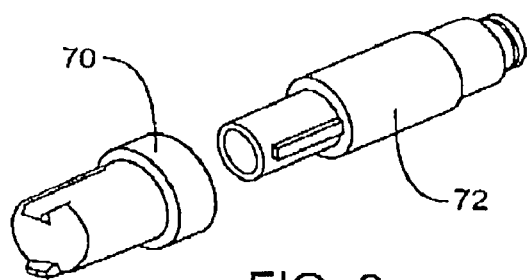
FIG. 8 is a perspective view of the mechanical limiter switch of the present invention, mounted on a substrate and assembled into a medical/surgical device which is mounted into a connector which can be mounted into a hand piece.

As previously discussed, the substrate 50 can be mounted in a hand piece or receptacle electrical connector 70, which is used in the medical/surgical procedure, and which after the procedure must be appropriately sterilized. The hand piece or receptacle electrical connector 70 is connected to a plug connector 72 as shown in FIG. 8. However, the switch 10 of the present invention can also be mounted in the plug connector 72 rather than in the hand piece or receptacle electrical connector 70. This is one application of the present invention.

Figure 9A:
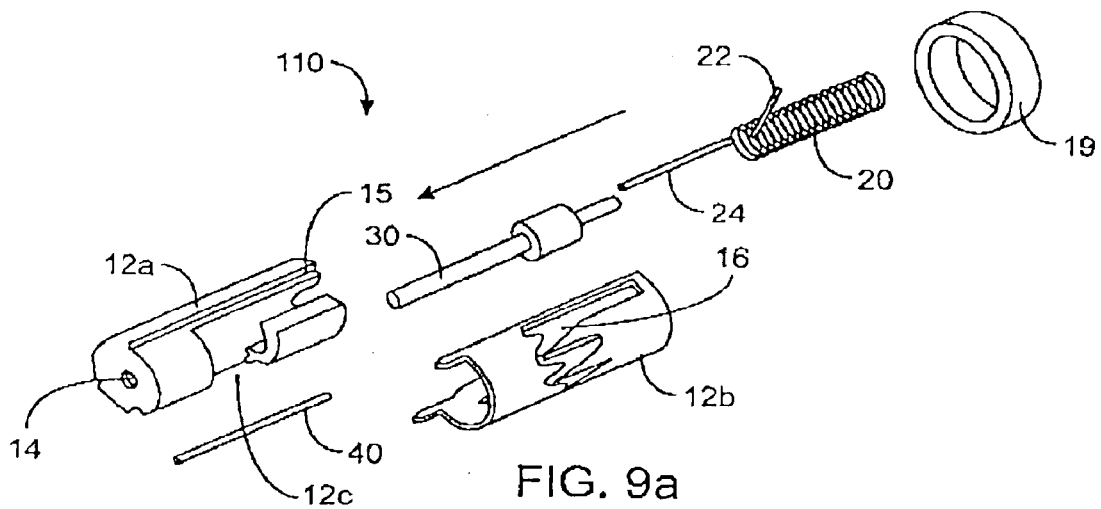
FIG. 9a is an exploded perspective view of another embodiment of the mechanical limiter switch of the present invention.
Figure 9B:
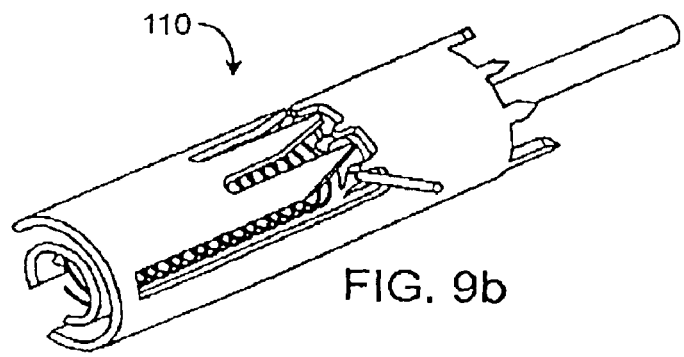

Referring to FIG. 9a, there is shown an exploded view of another embodiment of a switch 110 of the present invention. The switch 110 has many components similar to the components of the switch 10. The switch 110 comprises a housing 12 having two parts 12a and 12b. The first part 12a is made of plastic and is substantially cylindrically shaped. The housing 12a has a central axial opening 14, radial opening 12c, and a notch 15 along its axial direction. The second part 12b of the housing 12 is of metal and is a cover plate covering portions of the first part 12a, and having the pattern 16. A plunger 30 is mounted axially through the axial opening 14 of the housing 12. A spring 20 has a radially protruding member 22, near a first end. The second end 24 of the spring 20 is bent axially. The spring is mounted axially into the axial opening 14 of the housing 12, with the member 22 protruding through the pattern 16 of the second part 12b, and with the second end 24 in the axial notch of the first part 12a. A cap 19 encloses one end of the housing 12. A fully assembled switch 110 is shown in FIG. 9b. Functionally, the switch 110 works just like the switch 10. However, unlike the embodiment shown in FIG. 1, the switch 110 does not require an external contact pin 40 for operation. A contact pin 40 can be mounted within the housing 12 if it is desired to established electrical continuity when the member 22 contacts the pin 40. Alternatively, the contact pin 40 can be removed and the switch 110 operates so that electrical continuity is always established until the member 22 reaches a terminating position, at which point the electrical continuity is broken. The two methods of operation are explained as follows.

If it is desired to establish electrical continuity at the end of the traversal of the member 22, contact pin 40 is placed in the housing 12. The contact pin 40 is insulated from the conductive portion 12b of the housing 12. Electrical contact on the substrate 50 is established to the spring 20 and to the contact pin 40. In this manner, as the member 22 traverses the pattern 16, it establishes electrical continuity when the member 22 contacts the contact pin 40.

If it is desired to break electrical continuity at the end of the traversal of the member 22, contact pin 40 is removed from the housing 12. Electrical contact on the substrate 50 is established to the plunger and to the metal portion 12b of the housing 12. In this manner, as the member 22 traverses the pattern 16, it continually establishes electrical continuity with the metal portion 12b of the housing 12. When the member reaches its terminating position, it would contact the insulating portion 12a of the housing 12, thereby breaking electrical continuity.

Figure 10A:
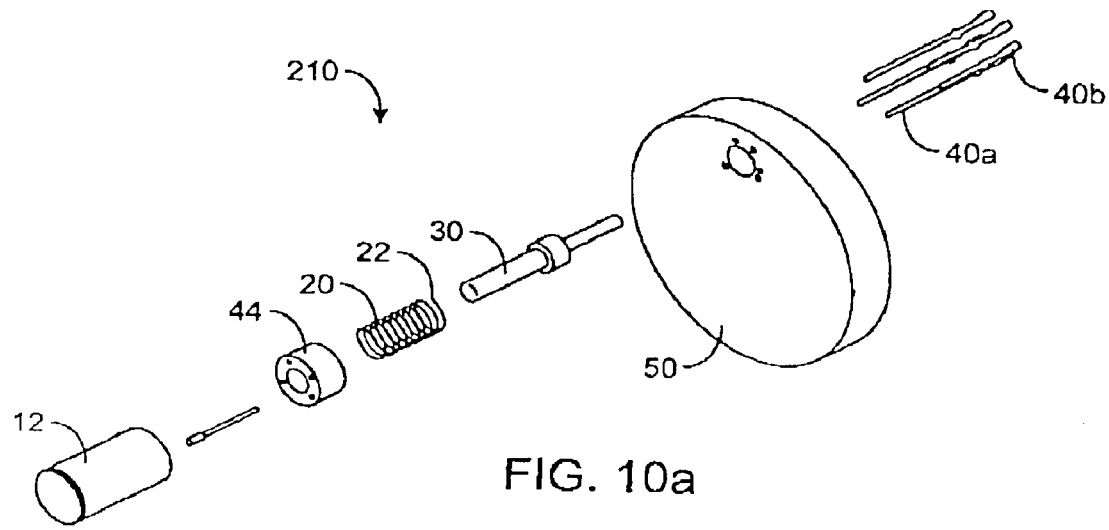
FIG. 10a is an exploded perspective view of yet another embodiment of the mechanical limiter switch of the present invention.
Figure 10B:
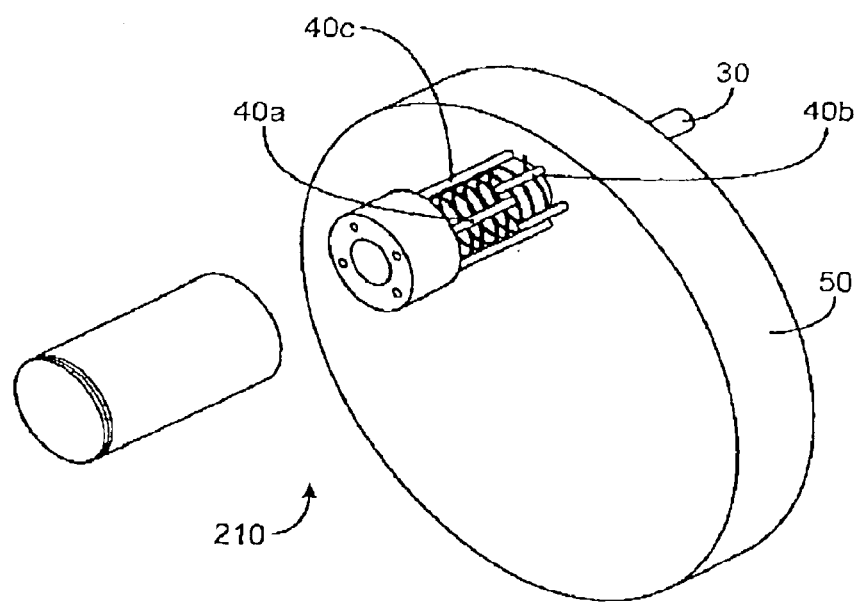

Referring to FIG. 10a there is shown an exploded perspective view of yet another embodiment of a switch 210 of the present invention. The switch 210 has many components similar to the components of the switch 10, and 110. The switch 210 is mounted on a substrate 50, which has an axial opening there through. A plunger 30 is mounted in the axial opening and urges a spring 20 against an end cap 44. The spring 20 has a radially protruding member 22, near a first end. The second end 24 of the spring 20 abuts the end cap 44. The spring 20 is mounted axially into the axial opening of the substrate 50. A plurality of posts 40a and 40b are positioned around the opening in the substrate and around the plunger 30. Some of the posts 40b are mounted on the substrate 50 and extend outward to the end cap 44. Some of the posts 40a are mounted on the end cap 44, and extend downward to the substrate 50. Thus, there exists a gap between the posts 40a and the posts 40b. One of the posts 40c extends from the substrate 50 to the end cap 44. The member 22 is positioned to protrude through the gap between the posts 40a and 40b and traverses the pattern formed by the gap until it reaches the end of its traversal and contacts the post 40c, which extends between the substrate 50 and the end cap 44. A housing 12 may enclose the end cap 44, the spring 20 and the posts 40a, and 40b. A fully assembled switch 210 is shown in FIG. 10b. Functionally, the switch 210 works just like the switch 10 or 110. However, unlike the embodiment shown in FIG. 1 or 9, the housing 12 does not have a pattern through which the member 22 protrudes and through which the member 22 traverses. Rather, the pattern is formed by the gaps between adjacent posts 40a and 40b, mounted on the substrate 50 and on the end cap 44 respectively. Further, because of the end cap 44, other electrical components, such as resistors and capacitors can be mounted on the end cap 44, and electrically connected to the various posts 40a, 40b or 40c, attached to the end cap 44. Similar to the operations described for the switch 10 or the switch 110, the switch 210 has two modes of operation. In a first mode, as the member 22 traverses the gap between adjacent posts 40a and 40b, it establishes electrical continuity, and at the end of its traversal when it contacts post 40c, electrical continuity is broken. The second mode of operation is where the member 22 traverses the gap between the adjacent posts 40a and 40b and establishes electrical continuity at the end of its traversal when it contacts post 40c. The two methods of operation are explained as follows If it is desired to establish electrical continuity at the end of the traversal of the member 22, the post 40c is made of a metal, and all the other posts 40a and 40b are made of an insulating material. Electrical contact on the substrate 50 is established to the plunger 30, which contacts the metal spring 30, and to the terminating post 40c. In this manner, as the member 22 traverses the gap between the posts 40a and 40b, it establishes electrical continuity only when the member 22 contacts the terminating posts 40c.

If it is desired to break electrical continuity at the end of the traversal of the member 22, the post 40c is made of an insulator, and all the other posts 40a and 40b are made of metal. Electrical contact on the substrate 50 is established to the plunger 30, which contacts the metal spring 30 and to all the other posts 40a and 40b. In this manner, as the member 22 traverses the gap between the posts 40a and 40b, it establishes electrical continuity with each of the posts 40a or 40b, and when the member 22 contacts the terminating posts 40c, it breaks electrical continuity.

Figure 11A:
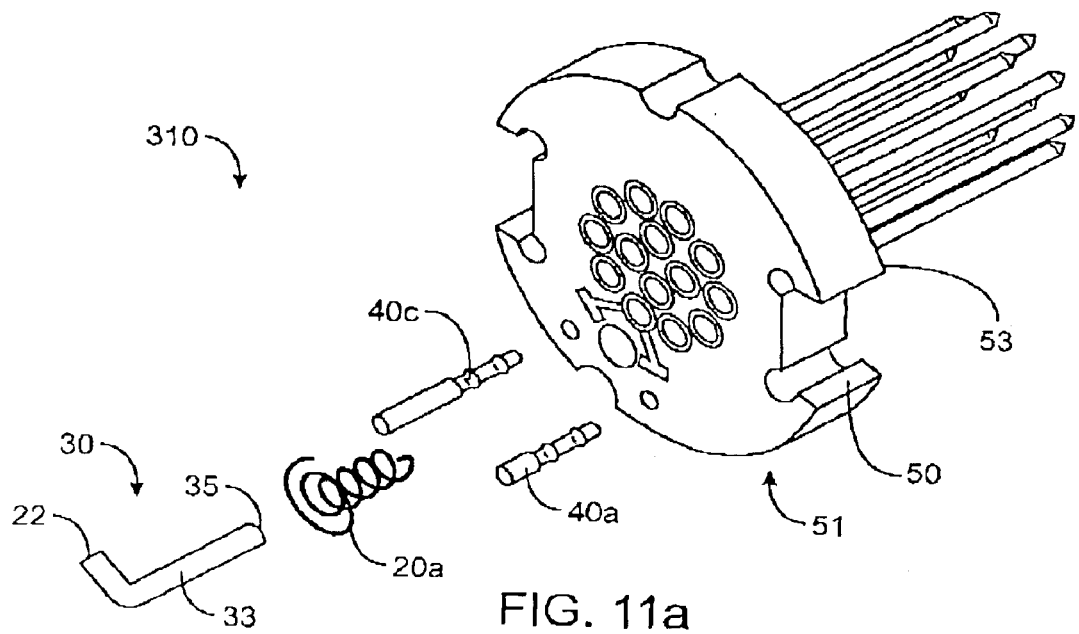
FIG. 11a is an exploded perspective view of still yet another embodiment of the mechanical limiter switch of the present invention.
Figure 11B:
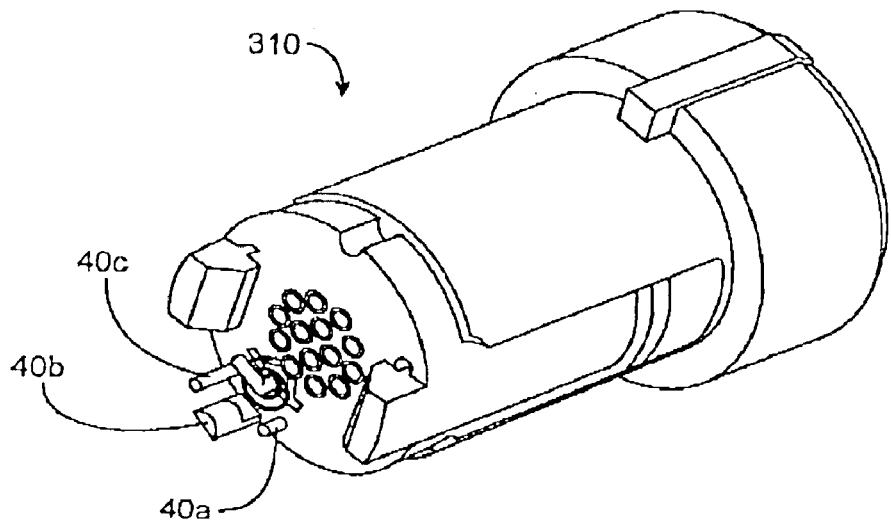

Referring to FIG. 11a there is shown an exploded perspective view of still yet another embodiment of a switch 310 of the present invention. The switch 310 has many components similar to the components of the switch 10, 110 and 210. The switch 310 is mounted on a first surface 51 of the substrate 50, which has an axial opening there through. A plunger 30 is mounted in the axial opening. The plunger 30 has two parts, a member portion 22, which extends substantially in a radial direction, and an axial portion 33. The axial portion has an end 35. The plunger 30 urges a first spring 20 against the first surface 51. The axial portion 33 of the plunger is positioned through the axial opening in the substrate 50. A retaining clip (not shown) is attached to the end 35 of the axial portion 33, thereby preventing the plunger 30 from coming out of opening in the substrate 50. A second spring (not shown) is positioned between the second surface 53 (the surface opposite the first surface 51) of the substrate 50 and the retaining clip. The second spring is stronger than the first spring 20a. Thus, when assembled the plunger 30 urges against the first spring 20a to the first surface 51 of the substrate 50. The first spring 20a is pre-tensioned to rotate in a radial direction. A plurality of posts 40a, 40b and 40c are mounted on the first surface 51 of the substrate 50 around the opening through which the plunger 30 is positioned. Each of the posts 40a, 40b and 40c can be of different sizes and of different material to accommodate the two modes of operation for the switch 310. A fully assembled switch 310 is shown in FIG. 11b. Unlike the switches 10, 110 or 210, there is no housing 12 whatsoever, nor any pattern through which the member 22 traverses. Similar to the switch 10, 110 and 210, the switch 310 can be operated in one of two modes. In a first mode, as the member 22 rotates and impinges the different posts 40a, 40b and 40c it establishes electrical continuity, and at the end of its traversal it breaks electrical continuity. The second mode of operation is where the member 22 rotates and establishes electrical continuity at the end of its rotation. The two methods of operation are explained as follows If it is desired to establish electrical continuity at the end of the rotation of the member 22, the post 40c is made of a metal, and all the other posts 40a and 40b are made of an insulating material. The post 40a is of low height such that after a use, and the hand piece or receptacle electrical connector 70 is withdrawn; the member 22 comes to rests against the first post 40a. When the hand piece 70 is again connected to the plug connector 72, the plunger is axially moved, causing the member to be at a height above the post 40a, thereby causing it to rotate to the member 40b. This continues until the member 22 comes to rest at the post 40c. The post 40c is of sufficient height such that further axial movement of the plunger 30 would not cause the member 22 to pass over the top portion of the post 40c. Electrical contact on the substrate 50 is established to the plunger 30 and to the terminating post 40c. In this manner, as the member 22 rotates, it establishes electrical continuity only when the member 22 contacts the terminating posts 40c.

If it is desired to break electrical continuity at the end of the rotation of the member 22, the post 40c is made of an insulator, and all the other posts 40a and 40b are made of metal. Electrical contact on the substrate 50 is established to the plunger 30 which contacts all the other posts 40a and 40b. In this manner, as the member 22 rotates, it establishes electrical continuity with each of the posts 40a or 40b, and when the member 22 contacts the terminating posts 40c, it breaks electrical continuity.

There are many advantages to the switch of the present invention. First, it relies entirely upon mechanical action to establish electrical continuity or to break established electrical continuity. Thus, it can withstand the rigor of x-ray or other harsh sterilization environment. It can be factory pre-set to limit the number of uses. It does not require changes to existing equipment, i.e. controller of the medical device to which it is attached. Indeed, if an external controller is used, it does not require changes to the external controller. It is small enough to fit within an existing device. Finally, the switch is inexpensive.

What is claimed is:

1. A mechanical limiter switch comprising:

A substantially cylindrically shaped housing having a perimeter and an opening in an axial direction; said housing having a pattern along said perimeter;

a spring mounted in said opening along said axial direction, and pre-stressed for movement in a radial direction and in the axial direction, said spring having a radial member protruding through said pattern; and a plunger mounted in said opening along said axial direction, abutting said spring for urging said spring in said axial direction and for moving said member in said pattern along said perimeter, to said contact pin;

wherein after a pre-determined number of activations of said plunger in said axial direction, said member comes to a terminating position.

2. The switch of claim 1 further comprising a contact pin in said housing at said terminating position, wherein said member contacts said contact pin at said terminating position, and electrical continuity is established.

3. The switch of claim 1 wherein said housing comprises a metal portion and an insulating portion, wherein electrical continuity is established between said plunger and said metal portion of said housing as said member traverses said pattern, and wherein said member, at said terminating position, contacts said insulating portion of said housing after said pre-determined number of activations of said plunger to break electrical continuity.

4. The switch of claim 1 wherein said housing further comprising a cap at one end of said opening, in said axial direction.

5. The switch of claim 1 wherein said spring has a first end and a second end, wherein said member is positioned near said first end; said spring further comprising a spring stop near said second end; said housing comprising a notch along said perimeter for holding said spring stop.

6. The switch of claim 1 wherein said pattern causes said spring member to pass there through in a substantially zigzag path.

7. The switch of claim 6 wherein said zigzag pattern determines the number of activations of said switch, and wherein said zigzag pattern comprises one or more crests and one or more troughs, wherein the distance between each crest and trough is determinative of the distance of throw of said switch and the amount of force required for each activation.

8. A mechanical limiter switch comprising:
a substantially cylindrically shaped first housing having a first radius, a perimeter and an opening in an axial direction; said first housing having a first pattern along said perimeter; a substantially cylindrically shaped second housing having a second radius, larger than said first radius, and a second perimeter, said second housing having a second pattern along said second perimeter; said second housing enclosing said first housing with said first pattern having a portion in common with said second pattern;
a spring mounted in said opening in said first housing along said axial direction, and pre-stressed for movement in a radial direction, said spring having a radial member protruding through said first pattern and second pattern; and
a plunger mounted in said opening along said axial direction, abutting said spring for urging said spring in said axial direction and for moving said member in said first and second patterns;
wherein after a pre-determined number of activations of said plunger in said axial direction, said member limits the operation of said switch.

9. The switch of claim 8 wherein said first housing is made of an insulator and said second housing is made of a metal, and wherein said member is limited in its axial direction of traversal by said first pattern and is limited in the radial direction of traversal by said second pattern and contacts said second housing, whereby electrical continuity is established.

10. The switch of claim 8 wherein said first housing is made of an insulator and said second housing is made of a metal, and wherein said member is limited in its axial direction of traversal by said second pattern and is limited in the radial direction of traversal by said first pattern and wherein during the axial direction of traversal said member establishes electrical continuity with said second housing, and wherein said member contacts said first housing at the end of its traversal and electrical continuity is broken.

11. The switch of claim 8 wherein said second housing is made of an insulator and said first housing is made of a metal, and wherein said member is limited in its axial direction of traversal by said first pattern and is limited in the radial direction of traversal by said second pattern and wherein said member establishes electrical continuity with said first housing during its traversal and contacts said second housing at the end of its traversal, whereby electrical continuity is broken.

12. The switch of claim 8 wherein said second housing is made of an insulator and said first housing is made of an electrical conductor and wherein said member is limited in its axial direction of traversal by said second pattern and is limited in the radial direction of traversal by said first pattern and wherein said member contacts said first housing at the end of its traversal and electrical continuity is established.

13. The switch of claim 8 further comprising a cap at one end of said opening, in said axial direction.

14. The switch of claim 8 wherein said spring has a first end and a second end, wherein said member is positioned near said first end; said spring further comprising a spring stop near said second end; said first housing comprising a notch along said first perimeter for holding said spring stop.

15. The switch of claim 8 wherein said pattern causes said spring member to pass there through in a substantially zigzag path.

16. The switch of claim 15 wherein said zigzag pattern determines the number of activations of said switch, and wherein said zigzag pattern comprises one or more crests and one or more troughs, wherein the distance between each crest and trough is determinative of the distance of throw of said switch and the amount of force required for each activation.

17. A mechanical limiter switch comprising:
a substrate;
a plurality of posts mounted on said substrate, spaced apart from one another forming an opening in an axial direction, with a pattern along the perimeter thereof having a termination position;
a spring mounted in said opening along said axial direction, and pre-stressed for movement in a radial direction, said spring having a radial member protruding through said pattern; and
a plunger mounted in said opening along said axial direction, through said substrate, abutting said spring for urging said spring in said axial direction and for moving said member in said pattern;
wherein after a pre-determined number of activations of said plunger in said axial direction, said member stops at said termination position and limits the operation of said switch.

18. The switch of claim 17 wherein each of said plurality of posts is of conductive material, and wherein said member establishes electrical continuity with each of said posts as said member traverses along said pattern, and wherein upon reaching said termination position, said member breaks electrical continuity with said posts.

19. The switch of claim 17 wherein each of said plurality of posts along said pattern is of an insulating material, and wherein upon reaching said terminating position, said member establishes electrical continuity.

20. The switch of claim 17 further comprising an end cap, and wherein a first alternating of said plurality of posts are attached to said end cap.

21. The switch of claim 17 further comprising a housing for enclosing said end cap, plurality of posts, and spring.

22. A mechanical limiter switch comprising:
a substrate;
a contact pin mounted on said substrate;
a housing mounted on said substrate, spaced apart from said contact pin, said housing having a perimeter and an opening in an axial direction; said housing having a pattern along said perimeter;

a spring mounted in said opening along said axial direction and pre-stressed for radial movement; said spring having a radial member protruding through said pattern;

a plunger mounted in said opening along said axial direction, abutting said spring for urging said spring in said axial direction and for moving said member in said pattern along said perimeter, to said contact pin;

wherein after a pre-determined number of activations of said plunger in said axial direction, said member will contact said contact pin.

23. The switch of claim 22 wherein after said member contacts said contact pin, electrical continuity is established.

24. The switch of claim 22 wherein further comprising a plurality of pins placed spaced apart from said housing, electrically connected together, wherein said member contacts each pin as said member traverses said pattern, and wherein said member contacts said contact pin to break electrical continuity.

25. The switch of claim 22 wherein said spring has a first end and a second end, wherein said member is positioned near said first end; said spring further comprising a spring stop near said second end; said housing comprising a notch along said perimeter for holding said spring stop.

26. The switch of claim 22 wherein said pattern causes said spring member to pass there through in a substantially zigzag path.

27. The switch of claim 26 wherein said zigzag pattern or pattern such that the spring member passes through the pattern in a substantially zigzag path determines the number of activations of said switch, and wherein said zigzag pattern comprises one or more crests and one or more troughs, wherein the distance between each crest and trough is determinative of the distance of throw of said switch and the amount of force required for each activation.

28. The switch of claim 22 for mounting in a medical or surgical device.

29. The switch of claim 28, wherein said substrate has said housing mounted to one side and a plurality of electrical signal connectors on another side.

30. The switch of claim 29 wherein said housing is mounted by press fit, surface mount, through-hole mounting, "mosquito" clip mounting, adhesive mounting, molded-in mounting, or snap-fit mounting into a preformed shape.

31. The switch of claim 29 wherein said plunger passes from said another side into said housing on said one side; wherein said electrical signal connectors have a first length protruding from said another side, and wherein said plunger has a second length protruding from said another side, wherein said second length is shorter than said first length.

32. A mechanical limiter switch comprising:

a substrate having an opening therein in an axial direction, with a first surface and a second surface, opposite said first surface;

a plurality of posts mounted on said first surface of said substrate, spaced apart from one another and around said opening;

a first spring mounted in said opening along said axial direction on said first surface, and pre-stressed for movement in a radial direction; and a plunger mounted in said opening along said axial direction, through said substrate, urged against said spring in said axial direction, said plunger having a contacting member portion rotatable about said axial direction;

a retaining clip holding said plunger on said second surface;

a second spring positioned between said retaining clip and said second surface, said second spring stronger than said first spring for holding said contacting member portion substantially near said first surface;

wherein after a pre-determined number of activations of said plunger in said axial direction, said contacting member portion stops at a termination position and limits the operation of said switch.

33. The switch of claim 32 wherein each of said plurality of posts is of conductive material, and wherein said contacting member portion establishes electrical continuity with each of said posts as said contacting member portion rotates, and wherein upon reaching said termination position, said contacting member portion breaks electrical continuity with said posts.

34. The switch of claim 32 wherein each of said plurality of posts along said pattern is of an insulating material, and wherein upon reaching said terminating position, said contacting member portion establishes electrical continuity.

35. A mechanical system for limiting the number of activations of an electrical system, comprising:

a housing;

a patterned opening extending in a radial direction around a portion of the housing;

an electrical contact member extending through the patterned opening;

a contact pin positioned adjacent to the housing; and a plunger disposed for axial movement in the housing, wherein the electrical contact member advances along through the patterned opening from an initial position to a terminating position at which the electrical contact member touches the contact pin when the plunger has been depressed a pre-determined number of times.

36. The system of claim 35, wherein the housing is cylindrical.

37. The system of claim 35, wherein the patterned opening is slotted.

38. The system of claim 37, wherein the patterned opening is zigzagged.

39. The system of claim 35, wherein the patterned opening comprises a plurality of pairs of troughs and crests, and wherein the number of activations is pre-determined by the number of pairs of troughs and crests.

40. The system of claim 35, wherein the electrical contact member touching the contact pin establishes an electrical continuity in the electrical system.

41. The system of claim 35, wherein the electrical contact member touching the contact pin breaks an electrical continuity in the electrical system.

42. The system of claim 35, wherein the electrical contact member is an end of a spring, and wherein the spring biases the plunger in an axial direction.

43. The system of claim 35, wherein the electrical contact member moves in a radial direction along through the patterned opening in the housing as the plunger moves back and forth in an axial direction in the housing.

44. The system of claim 35, further comprising:

a substrate, wherein the housing and the contact pin are mounted onto the substrate.

45. The system of claim 44, wherein the substrate is a printed circuit board.

46. The system of claim 44, wherein the housing is mounted to a top of the substrate, further comprising:

a plurality of signal pin connectors extending from a bottom side of the substrate, wherein an end of the plunger passes through the substrate and extends from the bottom side of the substrate.

47. The system of claim 46, wherein the plunger is configured to be depressed when received into a plug connector, such that one activation of the electrical system occurs each time the plunger is received into the plug connector.

* * * * *